United States Patent [19]

Dotzauer et al.

[11] Patent Number: 4,709,559

[45] Date of Patent: Dec. 1, 1987

[54] COOLING SYSTEM FOR RELATIVELY MOVABLE COMPONENTS

[75] Inventors: Peter Dotzauer, Buckenhof; Martin Schmidt, Emskirchen, both of Fed. Rep. of Germany

[73] Assignee: Siemens Aktiengesellschaft, Berlin and Munich, Fed. Rep. of Germany

[21] Appl. No.: 876,752

[22] Filed: Jun. 20, 1986

[30] Foreign Application Priority Data

Aug. 1, 1985 [DE] Fed. Rep. of Germany ....... 3527657

[51] Int. Cl.$^4$ .............................................. F25B 3/00
[52] U.S. Cl. ........................................ 62/499; 165/86; 378/200
[58] Field of Search ............. 62/514 R, 499; 165/86, 165/89; 378/15, 130, 141, 199, 200

[56] References Cited

U.S. PATENT DOCUMENTS

| 3,981,702 | 9/1976 | Eskeli | 62/499 X |
| 4,022,032 | 5/1977 | Nott | 62/499 |
| 4,115,697 | 9/1978 | Hounsfield et al. | 378/15 |
| 4,355,410 | 10/1982 | Sullins | 378/199 |
| 4,402,085 | 8/1983 | Distler et al. | 378/15 |
| 4,456,826 | 6/1984 | Forster | 62/514 R X |

FOREIGN PATENT DOCUMENTS

| 0081751 | 6/1983 | European Pat. Off. |
| 0109206 | 5/1984 | European Pat. Off. |
| 57-50673 | 3/1982 | Japan |
| 2026812 | 2/1980 | United Kingdom |
| 2034149 | 5/1980 | United Kingdom |

OTHER PUBLICATIONS

"Status of Diagnostic X-Ray CT: 1979", Boyd, IEEE Transactions On Nuclear Science, vol. NS-26, No. 2, Apr. 1979.

Primary Examiner—Albert J. Makay
Assistant Examiner—Steven E. Warner
Attorney, Agent, or Firm—Hill, Van Santen, Steadman & Simpson

[57] ABSTRACT

A cooling system for relatively movable components, such as a rotor seated for rotation with respect to a stationary component, includes a sealed channel in the stationary component disposed between the stationary component and the movable component, and an evaporator disposed within the sealed channel. The channel is filled with coolant, such as alcohol or oil, which is circulated by a pump in a closed circulation path. Heat is thereby conveyed from the system components to be cooled to the evaporator, and from the evaporator to a location where the heat can be dissipated without disturbing operation of the device. The cooling system is suitable for use, for example, in a computer tomograph for cooling the radiation detector.

2 Claims, 6 Drawing Figures

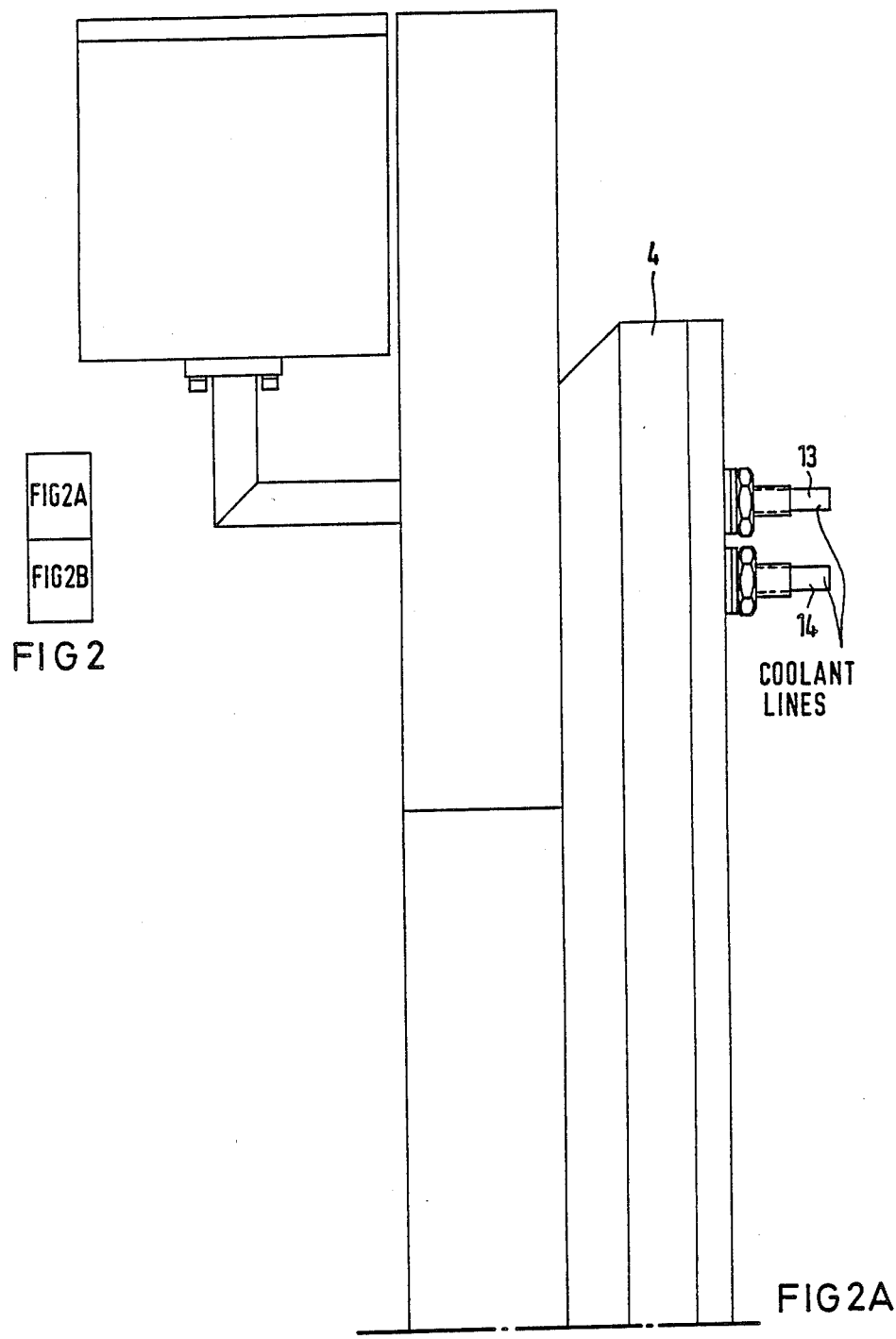

COOLING SYSTEM FOR RELATIVELY MOVABLE COMPONENTS

BACKGROUND OF THE INVENTION

The present invention relates to a cooling system for cooling a component which is movable relative to a stationary component, such as a rotor which is rotatably seated in a stationary device. In devices having stationary components as well as components relatively movable with respect to the stationary components, such as a computer tomograph, dissipating heat generated by the operation of the device must be undertaken at a location which does not disturb the intended operation of the device. In units such as computer tomography devices, a source of such heat is the leakage heat of the radiation detector and/or of the measuring electronics, which must be dissipated. Oil circulation can be provided for this purpose, with the cooling oil circulating between the components to be cooled and an oil cooler wherein the temperature of the oil is lowered, for example, by a ventilator. A problem is that the oil cooler in such an arrangement must be disposed on the movable part, i.e. the rotor, thereby causing substantial heating in the interior of the computer tomograph. Another problem is that localized heating, or heat pockets, may form. The sensitive measuring electronics are thus subjected to heat which can falsify readings and shorten the lifetime of the electronics.

SUMMARY OF THE INVENTION

It is an object of the present invention to provide a cooling system for a device having a movable part and a stationary part such that heat dissipation from the movable part can be undertaken at the exterior of the device.

The above object is achieved in accordance with the principles of the present invention in a device having a stationary portion with a sealed channel therein in which a movable component, such as a rotor, is rotatably seated. The evaporator of a cooling system is disposed within the sealed channel, and the channel is filled with a coolant in a closed circulating path on the rotor which contains the components to be cooled as well as a coolant pump. Heat arising in the rotor is conveyed into the channel between the stationary component and the rotor by the pumped coolant, and is conveyed to the exterior of the device by the evaporator disposed in the channel. The system is particularly suited for cooling the rotating radiation detector in a computer tomograph. The location at which the heat is actually dissipated into the atmosphere can be separated from the computer tomograph, so that the heat can be dissipated at a location which does not disturb operation of the tomograph.

DESCRIPTION OF THE DRAWINGS

FIGS. 2A and 2B, in combination as FIG. 2, are a side view, partially broken away, of the computer tomograph shown in FIG. 1.

DESCRIPTION OF THE PREFERRED EMBODIMENTS

Figure 1:
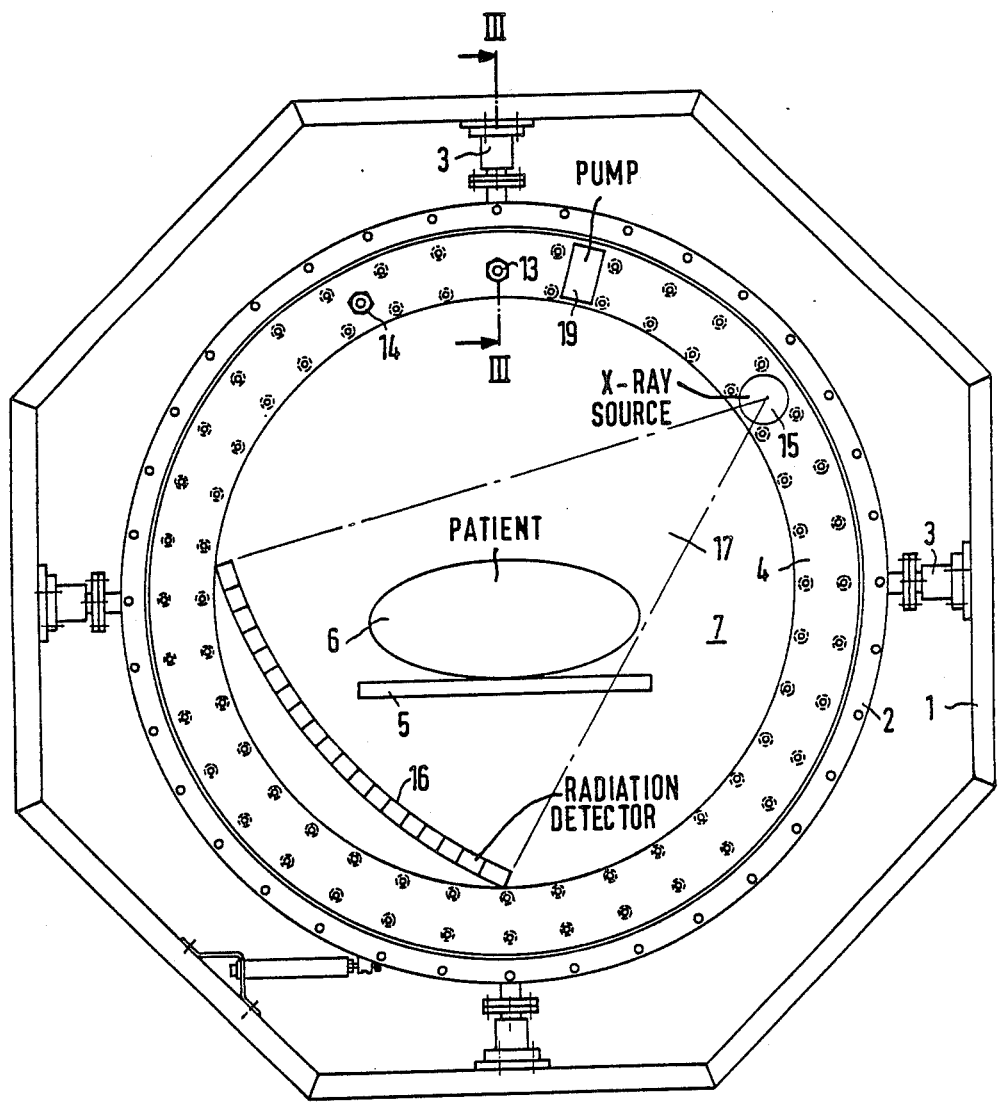
FIG. 1 is a side view of a computer tomograph having a cooling system constructed in accordance with the principles of the present invention.

A computer tomograph is shown in FIG. 1 having a frame 1 which forms a stationary part of the tomograph in combination with a ring 2. The ring 2 is supported in the frame 1 by a plurality of supports 3. An X-ray source 15 and a radiation detector 16 are rigidly connected to a rotor 4. The rotor 4 is mounted for rotation around the ring 2. The X-ray source 15 emits a fan-shaped X-ray beam 17 which transradiates a patient 6 lying on a patient support 5 within an examination space 7. The radiation detector 16 consists of a number of individual detector elements, each of which forms an output signal during rotation of the rotor 4 with the X-ray source 15 and the radiation detector 16 around the patient 6 through 360°. The signals from the elements within the detector 16 are supplied to a computer (not shown) which calculates a transverse slice image of the patient 6 based on those signals.

Figure 2B:
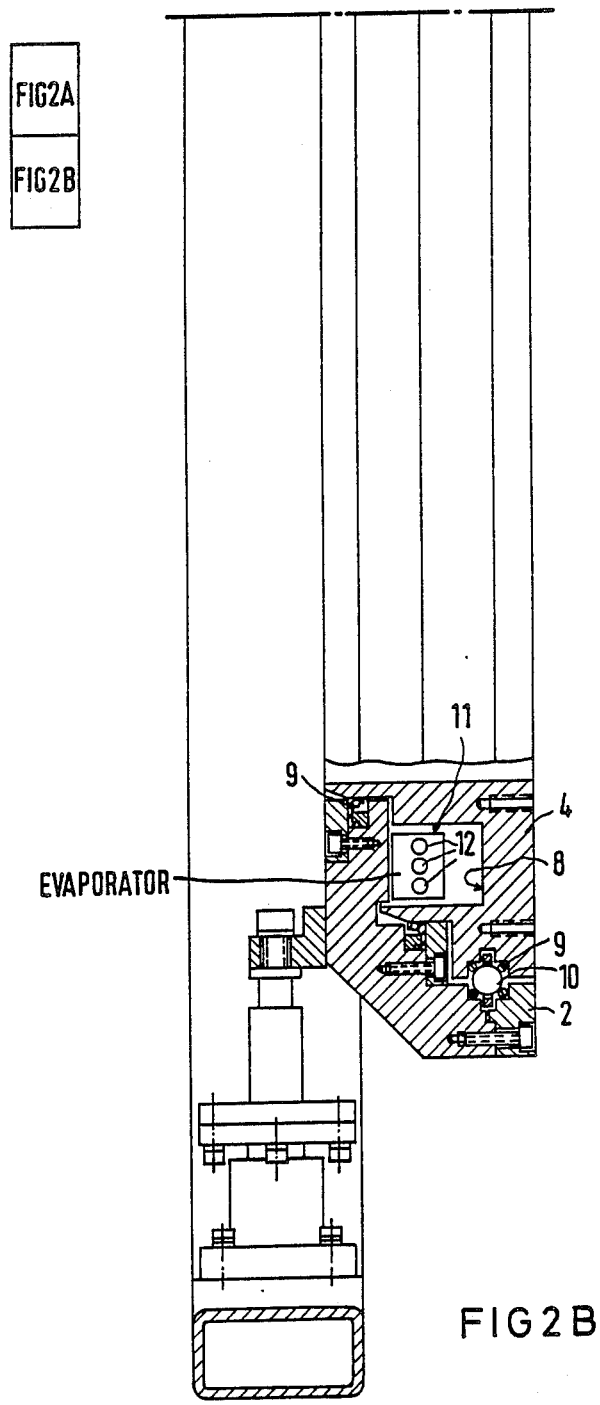
Figure 3:
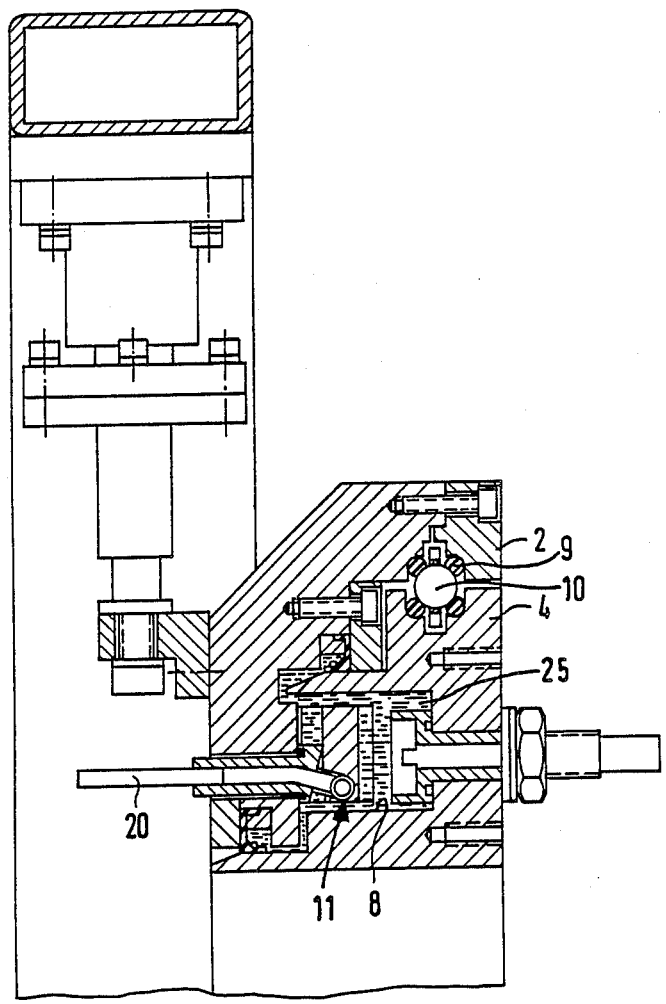
FIG. 3 is a sectional view taken along the line III—III of FIG. 1.

It is necessary to cool the radiation detector 16, particularly in computer tomography devices wherein continuous rotation of the rotor 4 occurs in order to achieve short scanning times. For this purpose, a channel 8, as shown in FIGS. 2A, 2B and 3, is provided between the ring 2 and the rotor 4. The channel 8 is sealed from the outside by sealing rings 9. A bearing 10 enables rotation of the rotor 4 relative to the ring 2. An evaporator for a cooling device is disposed within the channel 8. Three channels 12 of the cooling device for the coolant can be seen in FIG. 2B. The evaporator 11 is secured to the inside of the ring 2. The cooling device can be disposed at a stationary location next to the computer tomograph and connected to the evaporator 1 via suitable conduits.

The channel 8 is filled with a coolant, for example, alcohol or oil, which is supplied to the radiation detector 16 and is returned therefrom in a closed cooling circulation path on the rotor 4 by means of a pump 19. Two connections, 13 and 14, are shown in FIGS. 1 and 2A, which form the input and return lines for the coolant. The coolant conducts the heat generated by the radiation detector 16 to the evaporator 11, and the cooling device pumps the heat to a location where it can be dissipated into the atmosphere without disturbing operation of the tomograph.

Figure 4:
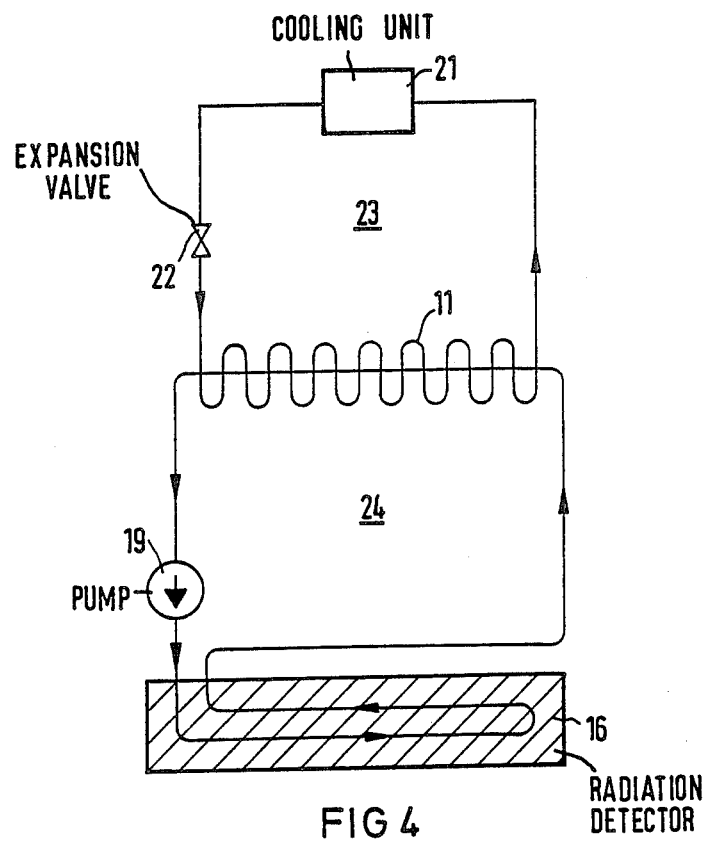
FIG. 4 is a schematic illustration of the circulation path for the cooling system constructed in accordance with the principles of the present invention shown in the above figures.

The channels of the evaporator 11 are connected to a separate cooling unit 21 shown in FIG. 4 via two nozzles, of which one nozzle 20 is visible in FIG. 3. As shown in FIG. 4, the cooling unit 21 is connected to the evaporator 11 by an expansion valve 21 and forms a closed stationary circulation path 23 with the evaporator 11. A rotating circulation path 24, which includes the coolant pump and the object to be cooled, i.e., the radiation detector 16, is operatively associated therewith.

The cooling system described herein permits the possibility of cooling a rotating component to which access along its rotational axis is not possible. The cooling system can be manufactured within broad size ranges of up to four meters in diameter. The cooling unit 21 can be mounted on flanges, for example, as a separate device. The object to be cooled is maintained at a substantially constant temperature, which can be selected within a broad temperature range.

Although modifications and changes may be suggested by those skilled in the art, it is the intention of the inventors to embody within the patent warranted hereon all changes and modifications as reasonably and properly come within their scope of contribution to the art.

We claim as our invention:

1. A cooling system for an apparatus having a stationary part and a movable part rotatably mounted with respect to said stationary part comprising:
   a sealed channel beteen said stationary part and said movable part,
   an evaporator disposed in said sealed channel disposed between the stationary part and the movable part;
   a cooling device connected with said evaporator;
   a closed cooling circulation path on said movable part including said channel;
   coolant filling said closed cooling circulation path; and
   a pump for circulating said coolant in said closed circulation path.

2. A cooling system as claimed in claim 1, wherein said movable part is a rotor for a computer tomograph carrying an X-ray tube and a radiation detector thereon, said rotor defining a space for receiving a patient therein, said X-ray tube and said radiation detector being disposed on both sides of said space in which said patient is received and said rotor having a movable cooling circuit therein forming a part of said closed circulation path.

* * * * *